United States Patent [19]

Pitz et al.

[11] Patent Number: 4,525,147
[45] Date of Patent: Jun. 25, 1985

[54] ROOT CANAL IMPLANT, PROXIMITY INDICATIVE, AND METHOD OF IMPLANTATION

[76] Inventors: Richard J. Pitz, 2 E. 65th St., New York, N.Y. 10021; Ezekiel J. Jacob, 25 Monroe Pl., Brooklyn, N.Y. 11201

[21] Appl. No.: 499,392

[22] Filed: May 31, 1983

[51] Int. Cl.³ .................................................. A61C 5/02
[52] U.S. Cl. .................................... 433/224; 433/228; 433/27
[58] Field of Search ................... 433/224, 27, 81, 226, 433/228, 201

[56] References Cited

U.S. PATENT DOCUMENTS

| 637,303 | 11/1899 | Tait | 433/224 |
| 720,394 | 2/1903 | Arndt | 433/224 |
| 1,463,963 | 8/1923 | Miller | 433/224 |
| 3,753,434 | 8/1973 | Pike et al. | 433/224 |
| 3,899,830 | 8/1975 | Malmin | 433/224 |
| 3,992,725 | 11/1976 | Homsy | 433/201 |

FOREIGN PATENT DOCUMENTS

| 2728494 | 1/1979 | Fed. Rep. of Germany | 433/224 |
| 2491326 | 4/1982 | France | 433/201 |
| 900844 | 1/1982 | U.S.S.R. | 433/224 |

Primary Examiner—John J. Wilson

[57] ABSTRACT

A root canal implant is proximity indicative by reason of its electrical conductivity and comprises carbon fibers. Method of implantation is by means of endogenous heating within the prepared dental cavity, of the implant, and is the preferred method.

5 Claims, 2 Drawing Figures

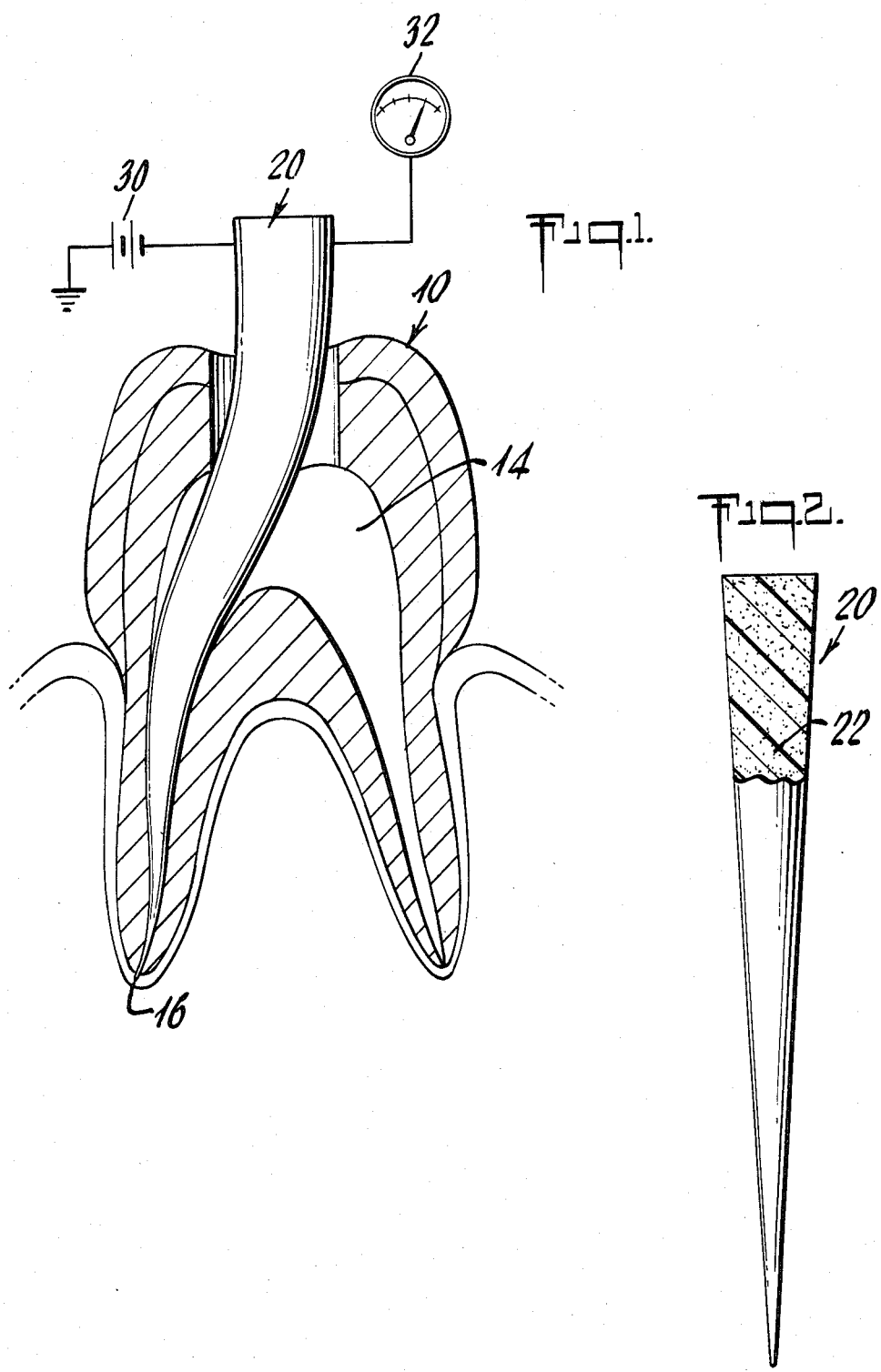

ROOT CANAL IMPLANT, PROXIMITY INDICATIVE, AND METHOD OF IMPLANTATION

PRIOR ART

NONE. A remote reference is from Chemical Week Aug. 9, 1978, page 49 "Making Dental Work Less Painful". Copy attached.

BACKGROUND OF THE INVENTION

ENDODONTIC DENTISTRY provides the background, based on current practice by experts practising in the field of root canal therapy. The endodontic dentist operates on a diseased tooth by opening up access to the canal. Then he debrides the canal which means the removal of all the soft tissue. Then he irrigates the canal to remove any pulpal remnants, any or most of the bacteria, then he enlarges the canal to remove any irregularities or rough surfaces on the inside of the canal, and the enlarging process is continued so that he can now put in a "POINT". A "point" is generally made of a thermoplastic material such as gutta percha, and is indeed referred to as a "GUTTA PERCHA POINT". Silver wire points are also used, but this is not within the purview of this invention. A Gutta Percha point as commonly used is made by "Indian Head Inc" in Switzerland. It consists of a thermoplastic thermoadhesive rod about 1½ inches long and varying in diameter from 0.010" to 0.090", different diameters being designated by different size numbers.

Many problems arise, which this invention seeks to overcome. One of the problems is repeated X-Rays in the mouth of the patient. X-Raying is always time-consuming and not always accurate, due to the anatomy at the end of the tooth and the angle at which the X-Ray is taken. The time of development and fixing, the X-radiation of progressive and successive X-Rays are all necessary to avoid the over-instrumentation of the canal, which means that the dentist must not force the implant material (the gutta percha point) inside the canal, past the apex of the tooth to create an irritant. But how is the proximity to the apex to be visualized other than by repeated and progressive in-tooth X-Rays? This invention provides an answer as specified in these specifications and in the drawings and claims. The dentist seeks accuracy. The end of the guttapercha "point" theoretically should terminate at the apex of the tooth or one mm. in front of the apex. Many times an X-Ray taken of the apex of the tooth shows the gutta percha point to be shy of the apex when it is actually touching the apex. This is due to the fact that the apex of the tooth is curved towards the film and the Gutta Percha point goes around and also follows the curvature of the root canal and is actually at the very end of the tooth. Many times, and in about 75% of the cases encountered by Dr. Pitz over sixteen years and about 4000 cases of root-canal surgery, the apex is not at the end of the tooth but somewhere off to the side. If the location is not accurate, then, and in the absence of intimate contact of the implanted gutta percha point with the white blood cells, and in the presence of the remnants of the pulpal tissue, or the presence of bacteria, there will be an antigen antibody reaction and anything might happen to traumatise the patient, from an apical scar, to a fulminating abscess, to a cyst. The new implant and the implantation technology invented here, permits the progression of the implant to be read by an electrical resistance reading offered by the conductive carbon fibers contained therewithin or thereabout, and as a final step an electrical force is applied to the same conductive fibers causing them to get heated hot. This heating is regarded as the endogenous heating capability of the new implant. By the application of electrical current, or supersonic vibrations the point will get heated by virtue of the carbon fibers therewithin. The amount of heating, the periods of heating are all controlled by the dentist during the progression of the point towards the apex of the canal. Simultaneously the proximity indicating capability of the point is utilised by an electrical meter reading. This endogenous capability ensures, in the hands of the trained dentist, that the inside of the canal is never overheated to cause tissue damage. The thermoadhesive point is finally tamped ("condensed") into place towards the end of the canal close to the apex. The point in its final place as electrically measured and in addition if desired, endogenously heated, is able to seal the entire root-canal with physiological elegance.

IMPLANTATION PROCESS

Conventional implantation may be used. Here the dentist heats the point in a flame to soften it. The surface softening is not enough to survive the heat loss suffered by external contact with the substance of the tooth. The point must have enough adhesiveness at its distal end to seal the apical area. A hand tool called the P.C.A. Inserter is used to push in the point. It has a large sphere of metal about 0.025" in diameter above the terminus of the instrument and removed therefrom. This instrument or a similar instrument provides a heat-sink or heat reservoir which is conducted to the terminus of the instrument. There is a failure inherent in this heat-sink type of instrument because of the relative difficulty of conducting heat applied to the proximal end of the implant to the extreme distal end while being heat-sealed to the apical area of the tooth canal.

The novel implantation process, applicable to this proximity indicating gutta percha point, is the implantation during the endogenous heating achieved by the point because of its carbon content or other resistance-heatable materials comprised therein, or thereabouts. Implantation during the endogenous heating utilises an outside electrical current applied to the fibers from proximal end to distal end. It may also utilise ultrasonic energy applied by means known to the ultrasonic art, at the proximal end of the implant during insertion. These instruments in the form of a miniature hammer or a horn are supplied by the Branson Sonic Power Company Danbury Conn. amongst others. The ultrasonic energy applicator may be combined with a drilling means so that there is the maximum effective energy available to be used selectively or in combination, for the root canal preparation and the implantation of the "point", and at some stage, the removal of detritus.

The carbon fibers confer the advantage of transmission through the point from proximal to distal end, with heat-softening achieved either wholly or partly by the ultrasonic action.

When endogenous heating is to be effectuated by the use of an electrical current to achieve electrical resistance heating several modalities are possible. Firstly, a terminal is attached to any part of the point, either along its entire length from proximal to distal and an electric current is furnished to heat the fibers, and by conduction, the circumambient gutta percha. Second, as a second alternative, terminals are attached to a selected portion of the length, and only this portion will undergo resistance heating, with the rest of the point acquiring heat by conduction in the unconnected portions. As a third alternative two points are used as a single point thusly: the distal ends are heat sealed with the fibers of each touching. The proximal ends provide the two terminals for the supply of electric energy. When this occurs, the distal end reaches great heat, probably because of a near short circuit. However, heating can be provided in any manner due to the endogenously heatable quality invented.

BRIEF DESCRIPTION OF THE DRAWINGS

FIG. 1:

The tooth 10 has a pulpal area 14. Pulpal area 14 has been evacuated and detritus removed. Canal containing pulpal area 14 shows one apex 16.

Into the tooth with its prepared root-canal is inserted the invented point 20. Point 20 indicates by electrical or electronic measurement and due to its inherent electrical conductivity as here invented, the position of its distal end with reference to the apex 16. Meter 32 is connected to the proximal end of the point 20. A power source 30 is provided.

FIG. 2:

This shows the "point". The general number of the figure is 20. Point comprises carboncontaining organic plastic 22.

EXAMPLES

Example #1:

A thermoplastic resin is coated on to Carbon Fiber Tow. The thermoplastic resin is Gutta Percha. The Tow is Celion ® Carbon Fiber K 3000 made by the Celanese Corp New York City N.Y. K 3000 signifies that there are 3000 filaments in the strand of tow. The Gutta Percha is pressure-extruded on the strand of tow using a short barrel 15:1 Rubber Extruder heated 200 F.-225 F.-250 F., the last heat being at the die. Upon cooling the coated Carbon fiber tow is compacted and bonded into a thin rod-shape about 0.013" in diameter. This rod, coated as described, is used as a root-canal implant for narrow root canals.

When inserted into the prepared and evacuated root canal, the distal end when it touches the apex of the tooth will show a conductivity of 40 micro-amps and will indicate to the dentist that optimal intrusion has been reached. At this point heat is applied to either end to soften the entire implant and cause it to thermoadhesively bond to and into the root canal. Meter readings will be different for different sets of conditions.

Example #2

The tow of example #1 is strip-coated using a strip-coating or "wire coating" die in a four heat-zoned 20:1 barrel. The coating does not completely embed itself around each fiber but is concentrated on the outside surface. The coated tow, when cooled will be a rod-shaped material, about 0.016" in diameter. The ends of the rod make better electrical contact at the apical end of the root canal. The rod is cut into 1.5 inch lengths for root canal implants. Apical indication is at 40 micro-amps approximately. The implant is then heated and caused to flow into and bond into the root canal. Heating may be by conventional means or by use of the endogenous heating capability of the implant as here disclosed, the heating continuing at any stage of implantation.

Example #3

This was a repeat of Example #1 except that the Gutta Percha was compounded with a filler in particulate form.

| GUTTA PERCHA: | 100 grams |
| --- | --- |
| Zinc Oxide, Lead-free | 50 grams |
| Inert Color | 3 grams |
| e.g. Red oxide Color ($Fe_2O_3$) | |
| $TiO_2$ | 0.5 grams |

Extruder temperatures were increased 5 degrees F. in the first and second zones and by 10 degrees F. in the final zone.

Example #4

This is an improvement on Example #3, in that the particulate filler is highly radioopaque in comparison with the other ingredients. Here Bismuth oxychloride was used.

| GUTTA PERCHA: | 100 grams |
| --- | --- |
| BISMUTH OXYCHLORIDE | 25 grams |
| Zinc Oxide, lead free | 25 grams |
| Inert color (e.g. $Fe_2O_3$) | 3 grams |

Extruder conditions are the same as Example #3. Virgin Stock is preferred here, because re-cycled or re-worked scrap showed a tendency to develop non-uniform coloration in the finished Gutta Percha Point.

Example #5

This is an improvement deriving from and pertaining to Examples 1,2,3,4, and succeeding examples where carbon fiber is used. It is the achieving of greater radioopacity of the Carbon Fiber component by plating said fibers with a metal.

| CARBON FIBER (Tow) Of Example 1 | ONE LENGTH |
| --- | --- |
| Metallized Carbon Fiber Tow | ONE LENGTH |

The lengths are placed alongside each other in any configuration. Thus one length may lie alongside the other and parallel thereto either contiguously or spaced therefrom. The disposition of the lengths may not only be in parallel fashion. They could be twisted together; intertwined; braided, or one length could be served with the other. The measurement of "one length" signifies that the filament content of the two can be widely different whether it be the Graphite fiber tow or the radiopaque metallized Carbon fiber tow, the more Carbon fibers, the more radiolucent, the more metallized carbon fibers the more radioopaque, and their relative proportions may vary from 0.5 to 99.5% and viceversa. In example that was specifically used as a benchmark we used an exact 1:1 ratio, there being 3,000 filaments in the length of Carbon Fiber tow, and 3,000 filaments in the length of the metallized Carbon Fiber Tow, and the same filamentary composition of the same denier was used:

| For the Graphite Fiber: | CELION ® 3000 K |
| --- | --- |

| | |
|---|---|
| For the Metallized Carbon Fiber: | Carbon Fiber sold by Celanese Corp. New York City N.Y. CORE FIBER was Celion ® 3000 K METAL PLATING was Nickel. Silver also was used, and is preferred in this Dental use. CHARACTERISTICS OF METAL PLATING: Coating is 0.5 Microns thick. Coating is 50% of total Fiber weight. |

While the metallized fibers are more radio-opaque than the Carbon fibers, due to the higher position of the Metals in the Atomic Table, compared with Carbon, we found that the electrical conductivity of the root-canal implant was improved. A comparative tabulation is as follows:

| | ELECTRICAL CONDUCTIVITY | |
|---|---|---|
| FIBER: | OHMS/CM. | OHMS/1000 strands/cm |
| Carbon | 0.36 | 4.27 |
| Nickel coated | 0.008 | 0.10 |
| Silver coated | 0.004 | 0.04 |

Gold coated fiber was also used, and this is the most radio-opaque, however, the metal coating can be of any metal cation, with the obvious exclusion of toxic metals and/or radioactive metals, and/or physiologically unacceptable metals, taboo for oral use.

Example #6

This concerns the use of Gutta Percha from Solvent suspension.

| | |
|---|---|
| Gutta Percha | 100 grams |
| Toluene | 200 grams |
| Methylene Dichloride | 200 grams |
| Acetone (or other Ketone) | 200 grams. |

Heat, mix, & dissolve. Use closed mixer in standard fire-proof techniques. The Gutta-Percha Lacquer is coated on to tow, in this case, the same tow used in Example 1, namely Celion ® Carbon Fiber 3,000K. The tow is coated in the manner of a wire enamelling machine, slightly modified, modification mainly designed to minimize abrasion of the fibers during handling. The first dip into the lacquer achieves compact rod-form bundling. The second and subsequent dips sizings will build up the coating so that the final root-canal implant conforms to the dimensions used in dentistry namely: (These are the popular sizes)

Gutta Percha "POINT" #5
Gutta Percha "POINT" #20
Gutta Percha "POINT" #25
Gutta Percha "POINT" #35

In this example and its modifications, the carbon fiber tow may be of any number of filaments, from 100 through 12,000 per strand of tow. Furthermore, the tow coated may be a composite of unmodified Carbon fibers and metal-plated carbon fibers, as explained in Example #6.

Example #7

The Solids material used in solution-coating of Example #6 comprises particulate material: For 100 Grams Gutta Percha substitute:

| | |
|---|---|
| GUTTA PERCHA | 50 grams |
| Zinc Oxide | 25 grams |
| Inert Color | 2 grams |
| TiO$_2$ | 1 gram |

Example #8

The solids material used in solution coating of Example #6 comprises particulate non-conductive material and particulate conductive material. Particulate conductive material may be used with or without other particulate materials. Particulate material with conductivity is selected from Conductive Carbon Black particles which may be either of Furnace black, Channel Black, Lamp black, or of Graphitic fibers, singly or in any combination.

For the graphitic fibrous particles, the source is Carbon Fiber chopped to a small size. representative materials being:

a. "THORNEL" ® Trade mark of the Union Carbide Corp Chicago Ill. 60606 (Fiber chopped to 0.040".)

b. "MAGMAMITE ®" Trade mark of the Hercules Corp, Wilmington Del. U.S.A. Fiber marked "MAGMAMITE ®", also a trade-mark of the Hercules Corp. Grade used was 1800/AS Chopped 0.250".

These relatively long fiber particles had the unusual result of making a better root-canal implant composition than the pulverised chopped "Thornel ®" which had a length of 0.040. The probable reason is that the Magmamite ®¼" fibers broke down during compounding to a satisfactory size, but in so doing, did it in a manner that maintained high conductivity, again postulating or surmising a reason that the slow separation of the fibers did not permit immediate encapsulation by the insulating Gutta Percha.

The coating formula thus is representative of other coating formulations and comprises: (for its solids component)

| FORMULA 8-1 | |
|---|---|
| Gutta Percha | 50 grams |
| Carbon Fiber particles | 10 grams |
| FORMULA 8-2 | |
| Gutta Percha | 50 grams |
| Acetylene Black (Conductive) | 20 grams |
| FORMULA 8-3 | |
| Solids of formula 8-1 | 50 gm. |
| Solids of formula 8-2 | 50 gm. |
| TOTAL: | 100 GRAM |
| Note: the proportions of 8-1 and 8-2 may vary with reference to each other from 1:100 down to 100:1. Fillers known in the art may be readily added, e.g. ZnO; TiO$_2$; Fe$_3$O$_4$ (black conductive) Fe$_2$O$_3$ (red iron oxide), to the limit of the cohesiveness and shape retentivity of the final Gutta Percha implant. | |
| Gutta Percha | 100 grams |
| Silver powder as used in Dental practice. | 5 grams to 100 grams + |

Increased percentage is for securing conductivity in the heavier cross-section sizes of the gutta percha points.
In place of or in addition to Silver powder, pulverized particles of other noble metals may be used, or particles of conductive organic plastics such as polyacetylene, polyferrocenes and the like.

Example #9

A straight-through extrusion process is used as an alternative to the coating of longitudinal carbon fibers, which are not used here. The much cheaper and more easy to handle chopped Carbon fibers are used. The chopped Carbon fibers are described in Example #8 above. A compound is devised as follows suitable for extrusion into strands or calendering into sheets or for pelletizing into a molding compound suitable for Injection Molding or for Compression Molding.

| GUTTA PERCHA | 100 Grams |
|---|---|
| Chopped Carbon Fiber | 5 to 300 Grams |
| Zinc Oxide, Lead free | 50 to 75 grams |
| Inert fillers for color | 5 grams |

Compounding is effected on a 6"×12" rubber and plastics Mill made by Reliable Machinery Co in N.J. The back roll is faster than the front roll. The rolls are heated to 180 degrees F. The Gutta Percha is thrown on to the mill, the fillers added gradually and the heat on the rolls being maintained to about 250 degrees F. Adiabatic (frictional) heat generates the additional heat. Use Scraper blade to strip off the highly sticky mass. Rolls are closed to 0.010", cooled and the compound is then easily cut off and stripped from the mill roll. Right after stripping the sheets are placed in a multiple platen slab cooler to cool down into a smooth flat sheet.

The compounds with the high percentage of Carbon Fiber to Polymer are used in heavy cross section root canal implants.

Furthermore, the subsequent processing of the compound will diminish the electrical conductivity until the final desired mechanical shape is fabricated. Where much grinding and shredding and mechanical shear is exerted as in extrusion, it is necessary to use the higher percentage Carbon fiber compound. The Final Products are thusly fabricated:

a. By rolling. This is the ancient method of producing the shape referred to in Example 6, where the sizes are given. The flat sheet produced by this example is slit into fine ribbons, about 0.050" wide. A ribbon is immersed into hot water (160 degrees F.), stretched and rolled between the fingers, or through the opening section of a rolling machine. The rolling machine, which may or may not be proprietary is fairly simple. There are two belts, one over the other and tensioned one over the other. One belt moves faster than the other and this differential speed produces a rubbing action which rolls the strip into a rod shape.

b. By extruding. A one-inch vertical extruder is mounted over a tank of cooling water under the surface of which is a conveyor belt. The Gutta Percha Compound is extruded through a spaghetti die as strands. These strands when cooled are dried by a cool air jet and chopped into 1½" lengths. A Foster-Allen Chopper is preferred from the many in the field. The Vertical extruder is made by Killion in New Jersey. It is electrically heated and thermostatically controlled in the heating zones and in the die-head.

c. By Injection Molding: The compound is chopped and fed into the hopper of the injection molding machine. Cooling time is necessary for a period longer than the conventional polyolefin and usual injection molding compounds, because in the case of this compound it is essential that the material be cooled from the hot state where it is sticky and amorphous, to the cool state when it becomes crystalline and hard. The phase change must take place before the molded point is stripped from the mold.

d. By Compression Molding: Press at 250 degrees F. until the mold halves close. Cool under confinement and remove. Heating is for the shortest time possible. With steam at 100 p.s.i. heating took 15 seconds. Mold was aluminum. Cooling with water at 55 degrees F. took 3 minutes. Press was 9"×12".

Example #10

This improved root-canal implant has a dual functionality. It retains its rod-form shape and stiffness while in contact with the environs of the apical end of the root-canal and continuously indicates the location and proximity of the apex, even after the gutta-percha is being softened and forced into intimate contact with the interior of the canal, with the action of heat and pressure from the dental compactor. After the filling and compacting process is on the way to completion, the distal end will begin to soften and fill the convoluted minute channels and passageways at the apical end. It retains its electrical proximity sensitivity almost to the end of the operation. To achieve this the central core consisting of carbon fiber filaments is given a primary coat of a resin solution applied and dried thereon. The priming coat comprises a resin which softens at a temperature higher than the enveloping gutta percha compound.

A suitable priming resin is gum Copal which has a long history of acceptance as an endodontic material. This priming resin is designed to melt after the gutta-percha around it melts, and amalgamate with the gutta percha when both are hot. If they are not compatible, as for example when the priming coat is made of collodion, there will be no amalgamation with the gutta-percha. Separation and exfoliation will take place. The Copal core is completely compatible with the gutta-percha. There are other resins which will achieve this dual-functionality root-canal implant. Preferred resins are: (amongst others)

a. Polyterpenes, m.p. 100 degrees C. "PICCOLYTE ®"

b. Hydrocarbon Resins-"PICCOPALE ®" 85 (85 deg.C.)

"Piccolyte ®" and Piccopale ® are trade marks of the Neville Co. Pittsburgh PA.

Around the prime-coated special purpose functionality-oriented Carbon fiber tow, are added coatings of a softer (135 F. to 160 F.) GuttaPercha. The Root-Canal Implant will retain its shape when heated and pushed into the root-canal. While the outside Gutta integument is soft, amorphous, thermoadhesive and flowing into the inner rugosities of the canal, the central fiber bundle is shape retentive. The dentist pushes it into the region of the apex, and the position is readable because of the conductivity of the still-intact bundle of fibers. Simultaneously, and "pari passu" the outside guttapercha has achieved softness and adhesion, thermoadhesively, to the inside of the canal at the proximal end of the invented 'point', and the heat is about to reach towards and soften the distal end. Then the distal end will reach its destination and be adhered in the apical area. The heating process amalgamates the inside stiff prime coating on the Carbon fibers with the outside Gutta Percha, and the entire implant will have been sealed in its cavity. The significant proximity-indicating aspect of this modification is that the distal end will not get soft till the near-termination of the operation, and therefore will not fold over upon itself, blocking further progress of the "point" towards the increasingly narrowing channels at the approaches to the apex. This example of the root canal implant may be referred to as the dual thermoplasticity implant, the thermoplasticity of the binder at the central core area being different from the thermoplasticity of the binder on the outside layers.

As a variation it is possible to use the same thermoplastic resin, but in two formulations. The first formulation is of a higher melting point than the second. The second, softer formulation is made by adding plasticizer to the first formulation; for example:

Binder for the central core carbon fibers: Gutta Percha

Binder for the outer part: Gutta Percha 100 parts with Ceresin Wax 10 parts, as plasticizer.

Example #11

This is a modification of Example #10. The binder around the central core fiber bundle resists heat softening as compared with the outer gutta percha, but this is achieved in a different fashion, by using a binder that is not a thermoplastic resin.

Said binder is an inorganic cement, namely cement such as Zinc Oxide-eugenol. The central core thusly bonded will permit intrusion into the root-canal because of its comparative rigidity under heating even past the temperature at which the outer gutta percha has achieved softening and heat flow under pressure. However the rigidity of the central fiber core is easily destroyed by additional pressure from the dental instrument applied during the penultimate stages of the operation. The formulation thus will be:

Binder for the central fiber core: ZnO-Eugenol
Binder for the outer section: Gutta Percha.

Example #12

In this example conductive carbon fibers are thermoadhesively impressed into any gutta percha point as continuous filaments extending from proximal end to distal end and on the outside surface of the point. The outside surface need not be completely enveloped by these longitudinal carbon fibers. A few filaments and theoretically a single filament affording contact with an electrical terminal at each end of the point and along its entire length will be sufficient. In practice, and due to difficult conditions of handling these fine filaments, about 10 to 1,000 filaments are used.

Example #13

A gutta percha point of conventional construction, as is commonly used in dentistry, is the starting material. Around this point is wrapped carbon fiber filaments in spiral fashion, serving as a conductive jacket all around the point. The wrapping is adhered into the outer surface of the point.

This jacketed point will conduct electricity from distal end to proximal end and will thusly have the apical proximity indicating feature claimed in this invention.

EXAMPLE #14

100% Solids Dental resin in liquid form: (curable) 100 gm
Chopped Carbon fiber See Example #8: 5 to 50 gm
Chopped metal plated Carbon fiber: (as X-Ray opacifier 2-25 gm.

A thermoplastic point is not used. Instead the fluid composition above, is injected into the root-canal with mild hydraulic pressure, and is converted into its final solid condition by heat or by any accelerator of the polymerisation reaction. What is referred to here as 100% solids resin is a trade term signifying that it is not a lacquer with a large proportion of liquid volatile solvents which evaporate and leave a void in their place. In dentistry Acrylic monomers, beta stage polymers, and other curable fluids are used capable of change from a fluid state to a solid state. One such system, also based on acrylic beta-stage resin appears in Chemical Week Aug. 9, 1978 and consists of "HYDRON ®" resin, made by the National Patent Development Corp, New York N.Y. X-Ray photos must still be considered necessary—see column 3 of the work cited—because there is no proximity indicating attribute in the filling material. In this example a dental casting resin is rendered proximity indicating by conversion into a composite comprising conductive Carbon Fibers, for the purpose of filling a root canal.

Example #15

In this embodiment a precursor sheet is made, and from it the finished points are chopped and rolled to size.

| | |
|---|---|
| Gutta Percha | 100 gm. |
| Zinc Oxide | 5 to 75 gm. |
| TiO$_2$ | 0.5 gm |
| Inert Color | 1 to 5 gm. |

Composition is compounded on a Rubber mill or in a Banbury or in a Masticator, or in a MILLSTRUDER ®. A Millstruder ® is a combination machine which is able to mix a compound in its mixing section and discharge it through a milling section between two mill rolls which press down and size the material as a sheet the width of the mill rolls. Clearance between the rolls determines the thickness of the sheet. The sheet is cooled and pressed flat. The thickness for the most desired finished points should be 0.010", as the thickness of the precursor sheet. In this state, carbon fiber filaments are laminated or otherwise adhered to the surface of the sheet as threads running mostly in the warp direction. As a modification, cover sheet of gutta percha is laminated or adhered to the top of the laminated fiber sheet thus creating a sandwich of carbon fiber threads between plies of gutta percha. The carbon fibers may be laminated in any direction or even incorporated as random fibers, and not confined to a warp direction. Either the sandwich of carbon fibers or the single ply lamination is then cut into strips the width of the desired gutta percha point size, and rolled into rod form if desired as in example #9. The points made in this way have uninterrupted electrical conductivity of the conductive carbon fibers from distal to proximal ends and are proximity indicative in functionality.

EXPLANATION OF THE EXAMPLES

A new dentistry has been created, of advantage to the patient. Root-Canal filling technology has been rendered expeditious, less costly, and with a minimum of X-Ray exposure to the patient. Conductivity of the root canal implant is the enabling means Reviewing the technique of root canal preparation, the dentist during instrumentation of the canal must know when to stop short of the apex. Step by step he enlarges the canal with a metal wire having cutting edges, (a "file") which also gauges and visualises and is visualised by X-Ray in the tooth as to its progression and location and depth. Repeated X-Rays of the file in the tooth are exposed during progression towards the apex. The file being metal is also used to indicate electrical readings which are translated to apical proximity readings. However it cannot go all the way in a dilacerated tooth, in most cases. Therefore the "File" cannot act as proximity indicator in such cases, locating the apex. It cannot act as a flexible sinuously proceeding conductor like the root canal implant herein specified in these specifications. It cannot be left in place. It cannot be heat-softened and adhered and condensed into the root canal, to be left in situ as a permanent root canal implant. Present point has all these modalities available to it. The electrical values attained at the conclusion of the insertion and close to the apex is approximately 40 microamps, for the file or for a silver wire point. The same meter gives the same values for the conductive point herein invented. One measuring device is called "FORMATRON" ® made by Parkell in N.Y. A better device is made by Ammident Corp in Pennsylvania. Other methods of electrical sensing and depth measurement are by means of eddy currents or by capacitance, and proximity to the apex can be measured by the very point which will later be heatsealed into the canal. Instead of a metal "file", as stated, a silver point may be used for proximity indication in the same way as metal file or the specified invented root canal implant is used. Silver wire point may indeed be left in the canal as a point and used in a manner similar to a gutta percha point. There is a defect inherent to the silver point however. It cannot be heat sealed in place. Objections may be catalogued thus:

Objection #1: The silver root canal implant is not thermoplastic nor is it thermoadhesive. It cannot be softened in the canal.

Objection #2: The silver root-canal implant will not make intimate contact with the inside of the root canal cavity, and therefore will permit the flow of bacteria past it and into the region of the apex Therefore the silver implant ("wire") must be cemented into place.

Objection 190 3: A cement, or dentally accepted Zinc Oxide-Eugenol is used, but is not efficacious because it does not lute the silver intimately to cementitious paste, and again fissures, cracks, passageways will form between the silver point and its peripheries and the rugosities of the root canal in which it has been cemented.

Objection #4: The silver point cannot be drilled out for a metal post preparation where indicated conditions for post exist.

Objection #5: The silver point is subject to galvanic corrosion in the electrolytic ambience of the oral cavity.

THE COMPARATIVE ADVANTAGES OF THE INVENTED POINT AGAINST SILVER

In answer to objection #1 above:
Invented point is thermoplastic and thermoadhesive. It can be softened to an adherable condition to bond to the inside cavities of the canal.

In answer to objection #2 above:
Invented root canal implant makes intimate adhesive contact with the irregular surface configuration of the canal. No bacteria can flow past it.

In answer to objection #3 above:
Invented point is highly conforming and heat-adherable. An interface of an incompatible cement is not needed. If Zinc-Oxide-Eugenol paste is used as a lining of the cavity, the softened adherable implant of this invention will amalgamate with the exposed profile of the surface of the cement pushing it strongly into the walls of the canal.

Heat-softening of the invented point is by conventional heating or by endogenous heating which occurs upon the application of external power. Silver points cannot be heated and if heated will serve no useful dental purpose. Silver is not thermoadhesive like a thermoplastic resin is.

In answer to objection #4 above:
Invented implant can indeed be drilled out for later post preparation. Drilling out is almost better and quicker than drilling out conventional gutta percha points, due to the presence of carbon fibers.

In answer to objection #5 above:
The carbon fibers comprising invented root canal implant are not subject to galvanic corrosion. They are extremely chemically inert. They provide in addition a conductive ambience within the canal contiguous to the canal walls. This conductivity is true tissue conductivity from wall to wall, whereas the silver point, which is conductive per se, does not provide a complete conductive ambience due perhaps to corrosion, insulation of its outside surface by the luting cement. It is accepted that a conductive environment is tissue-friendly. Known gutta percha points are non-conductive. Present invented gutta percha point is conductive.

In summary:
No dental implant in the endodontic root canal art provides the mechanical strength of the fibrous reinforcement, the fibers being inert chemically and biologically, the fibers being conductive, and the implant being proximity indicative when measured by instruments known and readily available. It can be heated from end to end or sectionally in any sectional part. It can be heated by electrical resistance within the tooth during the operation or outside the tooth. It can be heated ultrasonically within the tooth during the operation.

Sources of supply of carbon fibers:
Carbon fiber as used in this invention may be from any precursor base carbonaceous material, including, polyacrylonitrile fibers, Pitch; Cellulose; Coal. Composition of the fiber is not relevant as long as it has conductivity and chemical inertness.

Suppliers are:
Union Carbide Corp. Greenville S.C. Trade name "Thornel" ®;
Celanese Corp, Rock Hill S.C. Trade name "Celion" ®;
The Hercules Co, Magna Utah. Trade name "Magnamite" ®;

Toho Rayon Co Japan (selling through Celanese Corp);

Courtaulds Ltd. London England;

Dexter Corp, Windsor Locks, Conn. Hysol Division. T.M.="GRAFIL" ®.

Gutta Percha Equivalents: For the purposes of this invention, use:

Gutta percha is the trans polymer of Isoprene. It is a naturally occurring polymer, PALAQUIUM GUTTA. It analyses as 90% Hydro carbon for the best grade from Malaysia. An inferior grade is known as balata and is familiar in golf balls. It comes from a related tree in South America, MIMUSOPS BALATA.

Both Gutta percha and Balata may be used, separately or mixed in any ratio, the higher the Balata, the softer the mass.

Synthetic gutta percha

This is the trans polymer of Isoprene and is a synthetic product. It is sold by Polysar Corp, Sarnia, Ontario, Canada under the trade name of "TRANS PIP PP 301" ®

OTHER THERMOPLASTIC BINDERS FOR THE CONDUCTIVE CARBON FIBERS

1. Thermoplastic polymers of acrylic monomers, e.g. Butyl Methacrylate, Isobutyl methacrylate, mixed methyl methacrylate polymers 2. Styrenic block polymers, such as SBS, SIS,S-hydrogenatedbutadiene-S 3. Polyester thermoplastics, such as "Santoprene" ® sold by Monsanto Co. Akron Ohio 4. Ethylene polymers and terpolymers The precondition is thermoplasticity corresponding to the range of gutta percha to which dental techniques are adapted by ancient usage, and also freedom from physiological irritants. The contained carbon fiber in the finished thermoplastic implant being very chemically inert will not contribute to the catalytic breakdown of the polymer, to reversion, to embrittlement and the like.

What is claimed is:

1. A dental root canal implant comprising a unitary structure of thermoplastic resin and electrically conductive carbon fibers, whereby said implant is capable of conducting electricity for measuring the proximity of the implant to the apex of a root canal and for heating the thermoplastic resin.

2. A dental process for root canal therapy comprising:
   a. preparing the canal of a tooth,
   b. inserting a root canal implant comprising a thermoplastic resin and electrically conductive carbon fibers,
   c. heating to a thermoplastic adhesiveness said resin by heat generated in the fibers by application of energy thereto,
   d. condensing the implant intimately to the inside of the canal, and
   e. cooling said implant to room temperature.

3. The process of claim 2 wherein the heat is generated by electrical energy.

4. The process of claim 2, wherein the heat is generated by ultrasonic energy.

5. A process for measuring and filling a root canal comprising, inserting a thermoplastic rod having means to conduct electricity into a root canal, measuring the proximity of said rod to the apex of the canal, by an electrical measurement using said rod, converting said rod into a softened thermoadhesive mass by heating, intimately condensing the softened mass into the canal, and allowing said mass to cool and remain as a permanent implant.

* * * * *